US006268916B1

United States Patent
Lee et al.

(10) Patent No.: US 6,268,916 B1
(45) Date of Patent: Jul. 31, 2001

(54) SYSTEM FOR NON-DESTRUCTIVE MEASUREMENT OF SAMPLES

(75) Inventors: Shing Lee, Fremont; Mehrdad Nikoonahad, Menlo Park; Xing Chen, San Jose, all of CA (US)

(73) Assignee: Kla-Tencor Corporation, San Jose, CA (US)

( * ) Notice: Subject to any disclaimer, the term of this patent is extended or adjusted under 35 U.S.C. 154(b) by 0 days.

(21) Appl. No.: 09/310,017

(22) Filed: May 11, 1999

(51) Int. Cl.$^7$ .............................. G01J 4/00; G01N 21/00
(52) U.S. Cl. .......................................... 356/369; 356/432
(58) Field of Search .................................. 364/364, 369, 364/432; 386/381, 382

(56) References Cited

U.S. PATENT DOCUMENTS

| | | |
|---|---|---|
| 4,255,971 | 3/1981 | Rosencwaig . |
| 4,521,118 | 6/1985 | Rosencwaig . |
| 4,522,510 | 6/1985 | Rosencwaig et al. . |
| 4,679,946 | 7/1987 | Rosencwaig et al. . |
| 4,854,710 | 8/1989 | Opsal et al. . |
| 4,952,063 | 8/1990 | Opsal et al. . |
| 5,042,952 | 8/1991 | Opsal et al. . |
| 5,074,669 | 12/1991 | Opsal . |
| 5,149,978 | 9/1992 | Opsal et al. . |
| 5,206,710 | 4/1993 | Geiler et al. . |
| 5,228,776 | 7/1993 | Smith et al. . |
| 5,298,970 | 3/1994 | Takamatsu et al. . |
| 5,536,936 | 7/1996 | Drevillon et al. . |
| 5,608,526 | 3/1997 | Piwonka-Corle et al. . |
| 5,706,094 | 1/1998 | Maris . |
| 6,008,906 | * 12/1999 | Maris ................................. 356/432 |

OTHER PUBLICATIONS

"A New Method of Photothermal Displacement Measurement by Laser Interferometric Probe Its Mechanism and Applications to Evaluation of Lattice Damage in Semiconductors," S. Sumie et al., *Jpn. J. Appl. Phys.*, vol. 31, Part 1, No. 11, Nov. 1992, pp. 3575–3583.

"Effects of ambient gas on photo–acoustic displacement measurement by laser interferometric probe," S. Sumie et al., *J. Appl. Phys.*, vol. 74, No. 11, Dec. 1, 1993, pp. 6530–6533.

"Characteristics of photoacoustic displacement for silicon damaged by ion implantation," H. Takamatsu et al., *J. Appln. Phys.*, vol. 78, No. 3, Aug. 1, 1995, pp. 1504–1509.

"Analysis of lattice defects induced by ion implantation with photo–acoustic displacement measurements," S. Sumie, *J. Appl. Phys.*, vol. 76, No. 10, Nov. 15, 1994, pp. 5681–5689.

"Photodisplacement Measurement by Interferometric Laser Probe," H. Takamatsu et al., *Japanese Journal of Applied Physics*, vol. 29, No. 12, Dec. 1990, pp. 2847–2850.

"Photoellipsometry determination of surface Fermi level in GaAs (100)," Y. Xiong et al., *J. Vac. Sci. Technol. A*, vol. 11, No. 4, Jul./Aug. 1993, pp. 1075–1082.

(List continued on next page.)

*Primary Examiner*—Frank G. Font
*Assistant Examiner*—Zandra Smith
(74) *Attorney, Agent, or Firm*—Skjerven Morrill Macpherson LLP

(57) ABSTRACT

The surface of a doped semiconductor wafer is heated locally by means of a pump beam whose intensity is modulated at a first frequency. The heated area is sampled by a probe beam whose intensity is modulated at a second frequency. After the probe beam has been modulated (reflected or transmitted) at the first frequency by the wafer, the modulated probe beam is detected at a frequency equal to the difference between the harmonics of the first and second frequencies to determine dose of the dopants in the wafer. Such or similar type of instrument for measuring dose may be combined with an ellipsometer, reflectometer or polarimeter for measuring dose as well as thickness(es) and/or indices of refraction in a combined instrument for measuring the same sample.

69 Claims, 6 Drawing Sheets

OTHER PUBLICATIONS

"Photoellipsometry: a modulation spectroscopy method applied to n–type GaAs," Y. Xiong et al., *Thin Solid Films*, 234 (1993), pp. 399–401.

"Modulated ellipsometric measurements and transfer–matrix calculation of the field–dependent dielectric function of a multiple quantum well," J. Zettler et al., *Physical Review B*, Dec. 15, 1992, pp. 955–962.

Ellipsometric measurement of the Kerr magnetoopic effect, H. Minden, *Applied Optics*, vol. 18, No. 6, Mar. 15, 1979, pp. 813–817.

Ion Dose Monitor PA–400, Ion Implant Dose Measurement Systems, product brochure for Kobelco, Kobe Steel Ltd., 4 pages.

International Search Report dated Aug. 4, 2000.

* cited by examiner

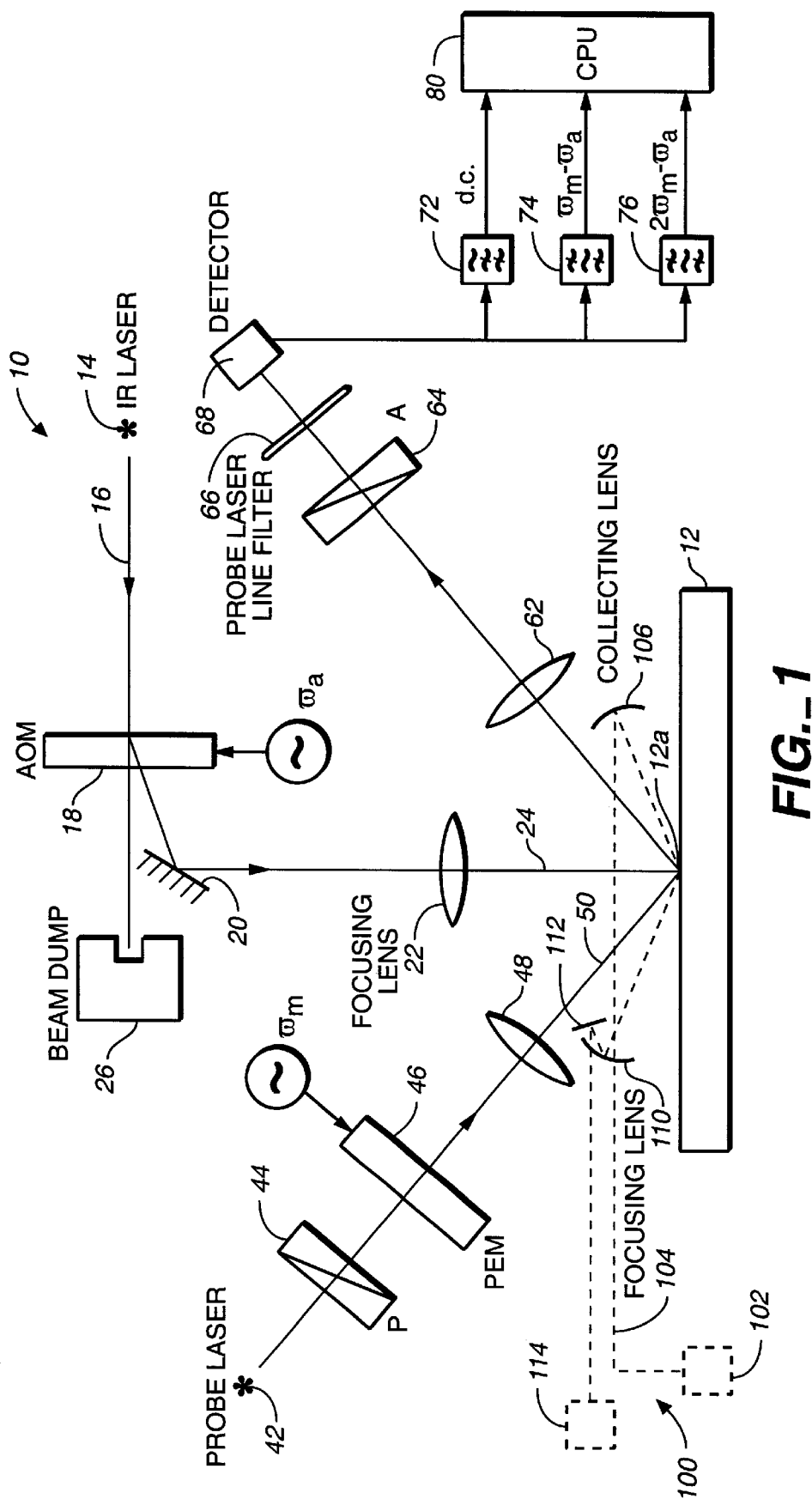
FIG._1

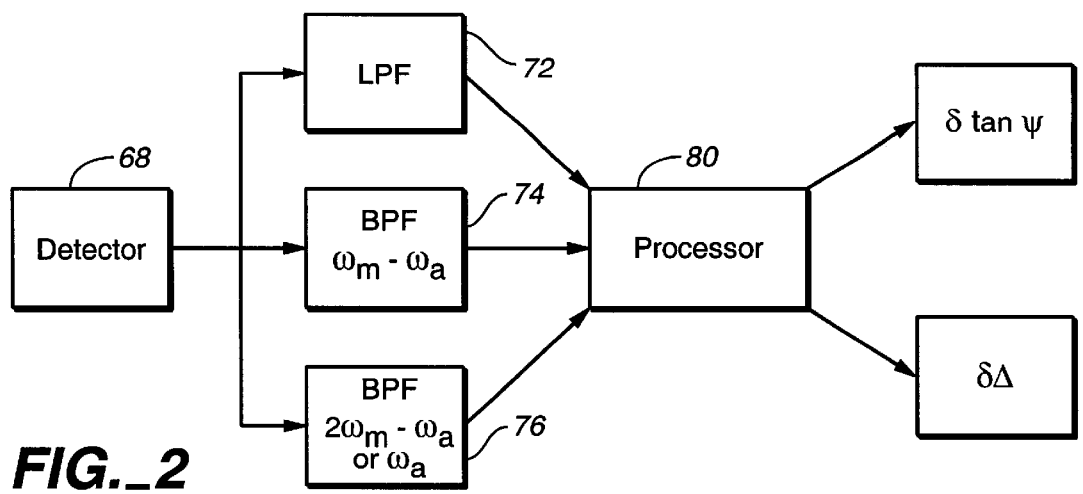
FIG._2
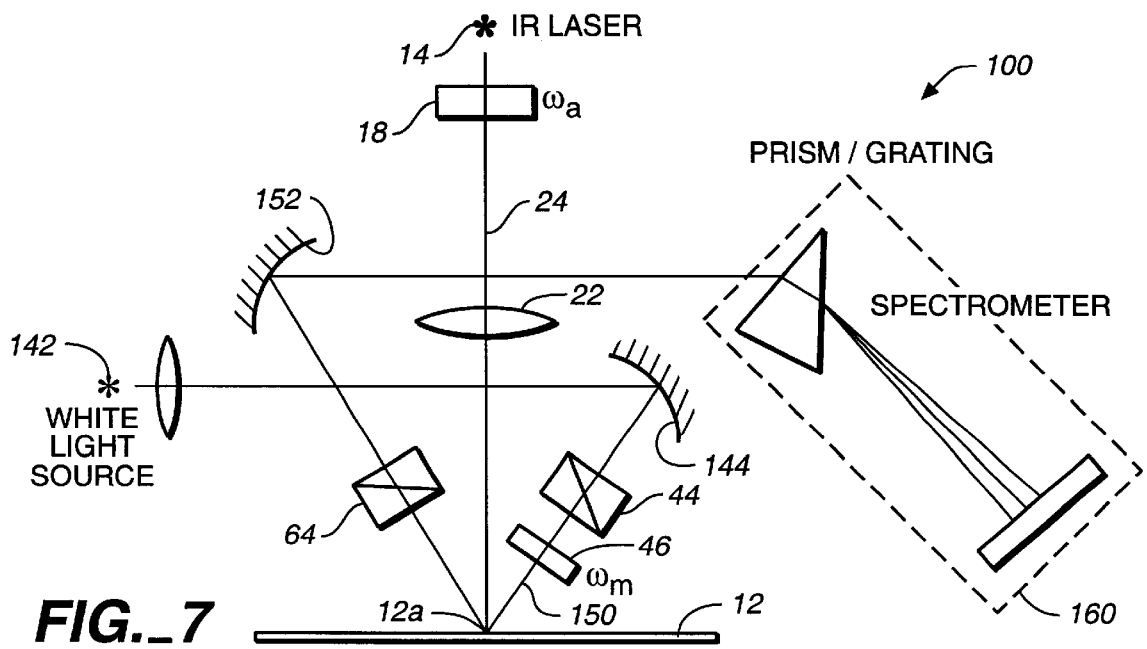
FIG._7
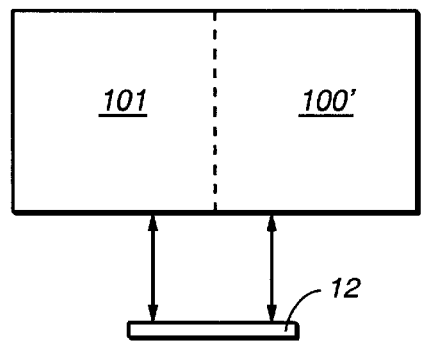
FIG._8

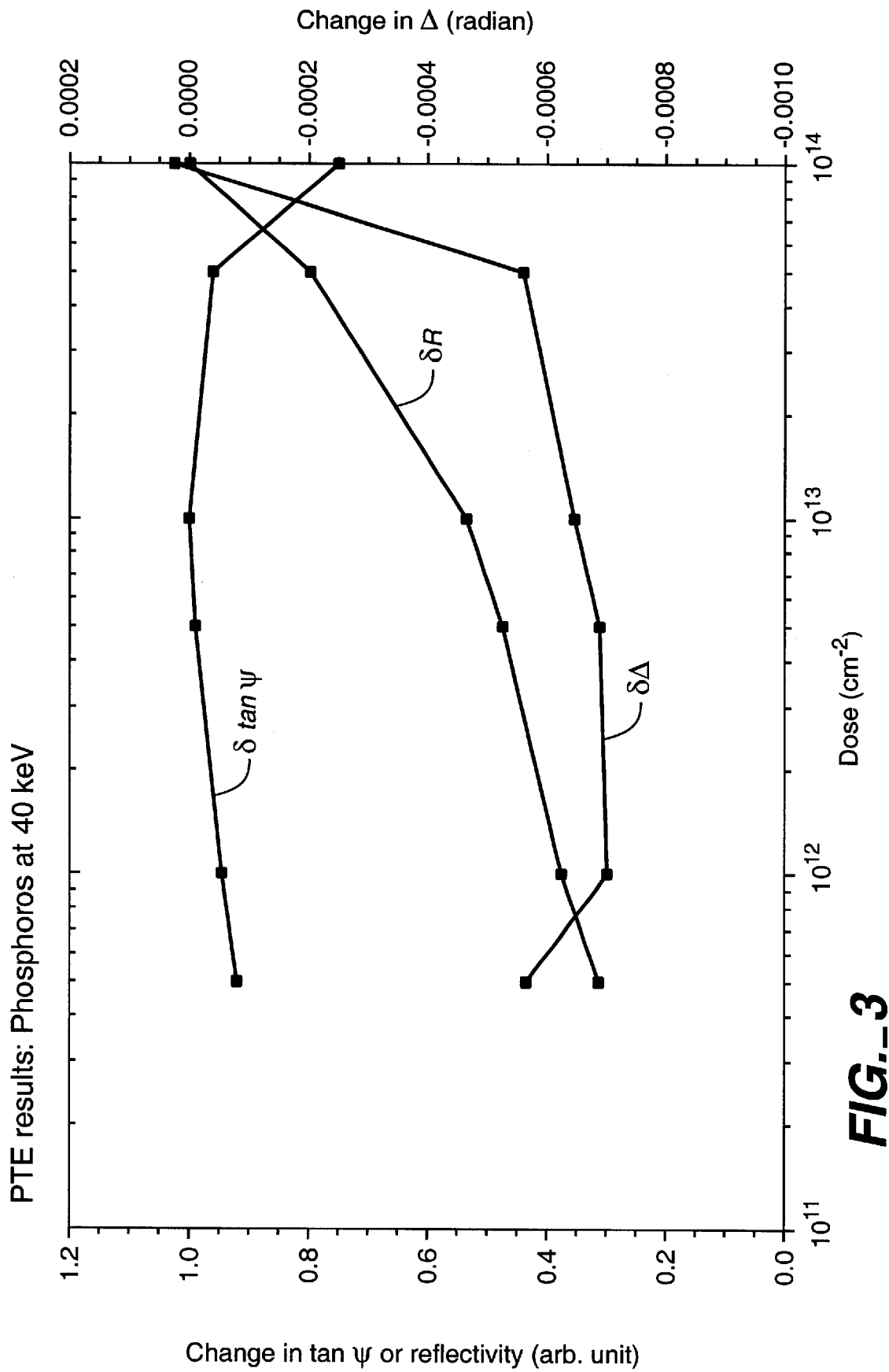
FIG._3

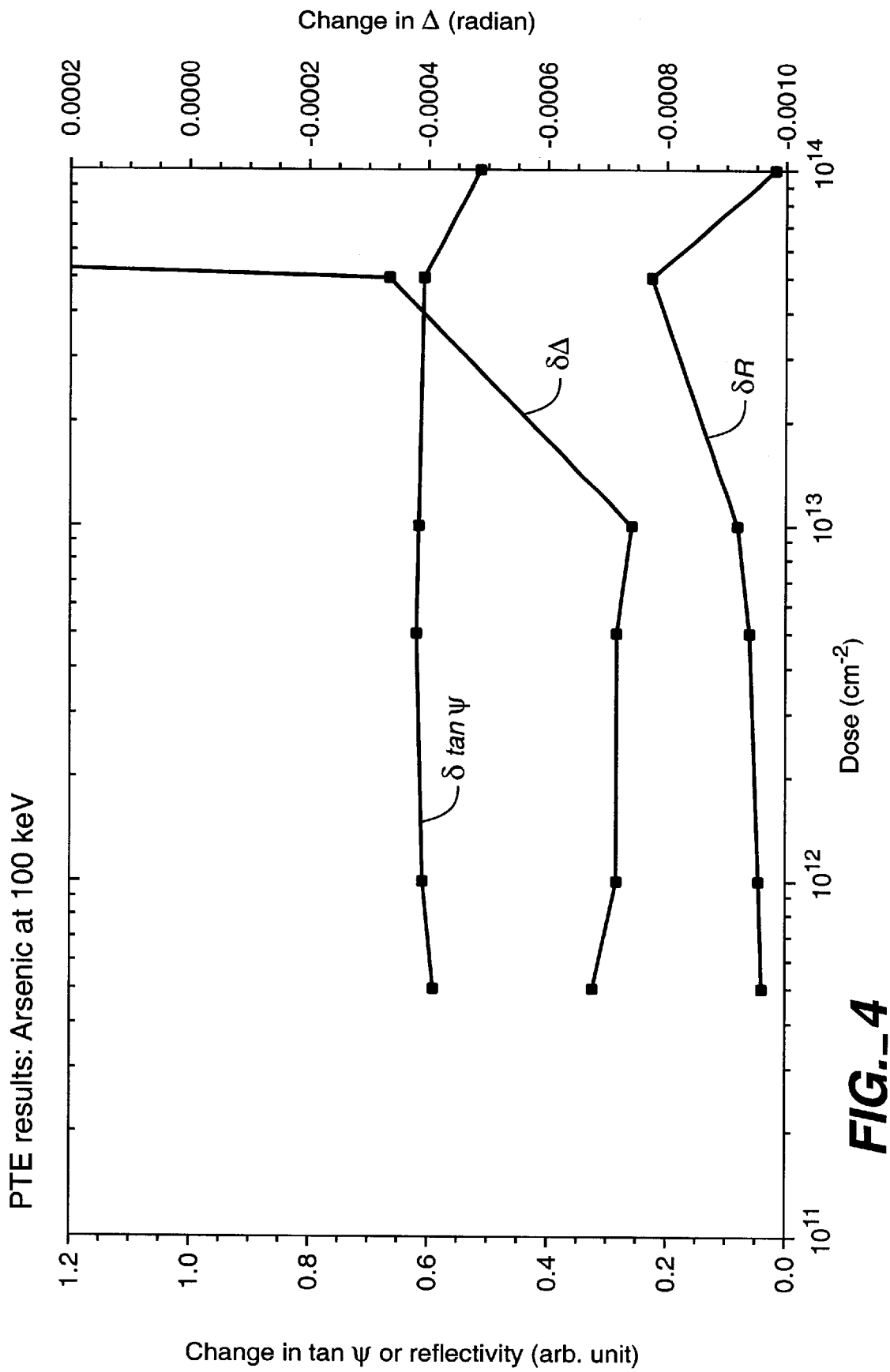
FIG._4

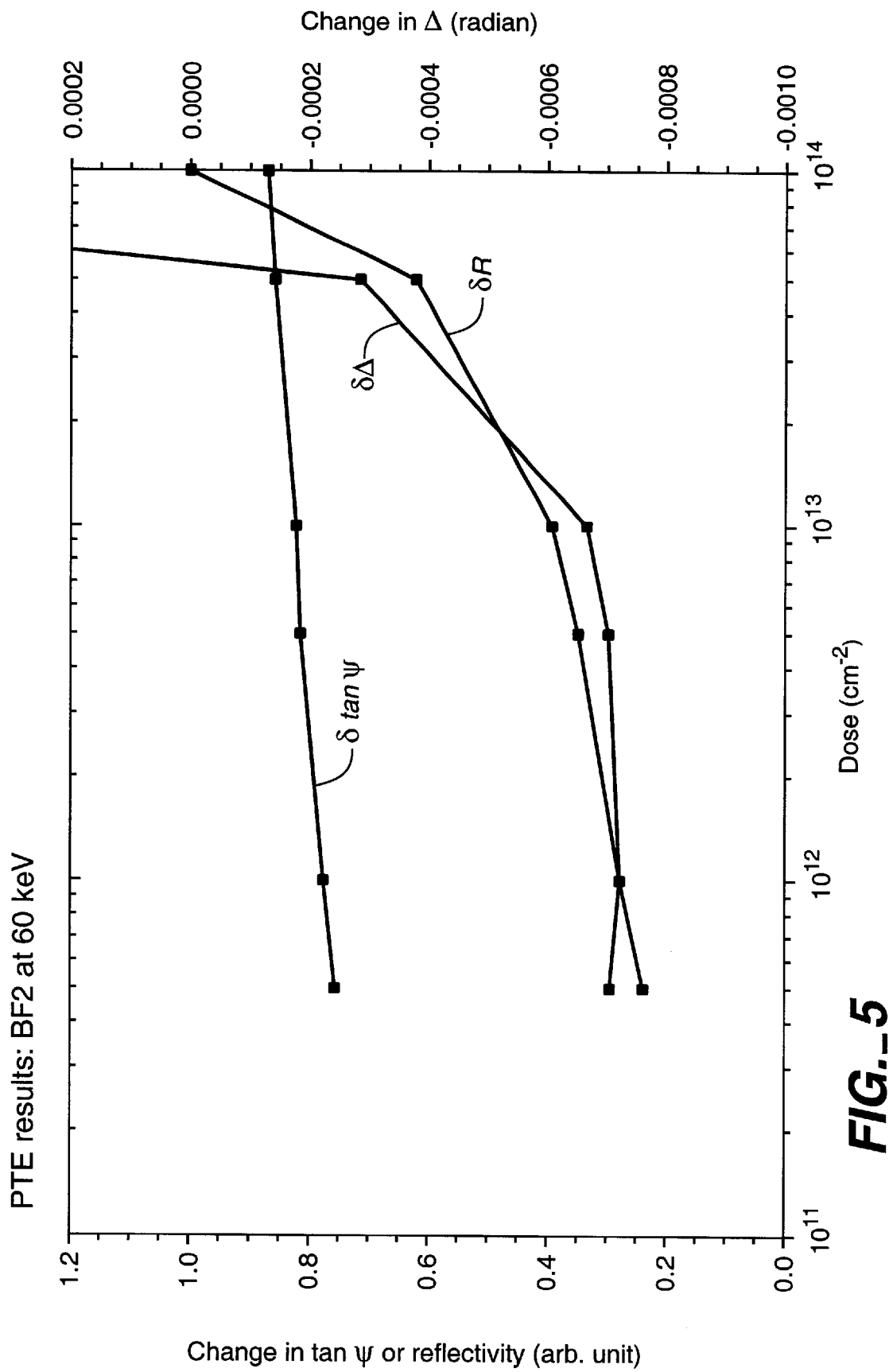
FIG._5

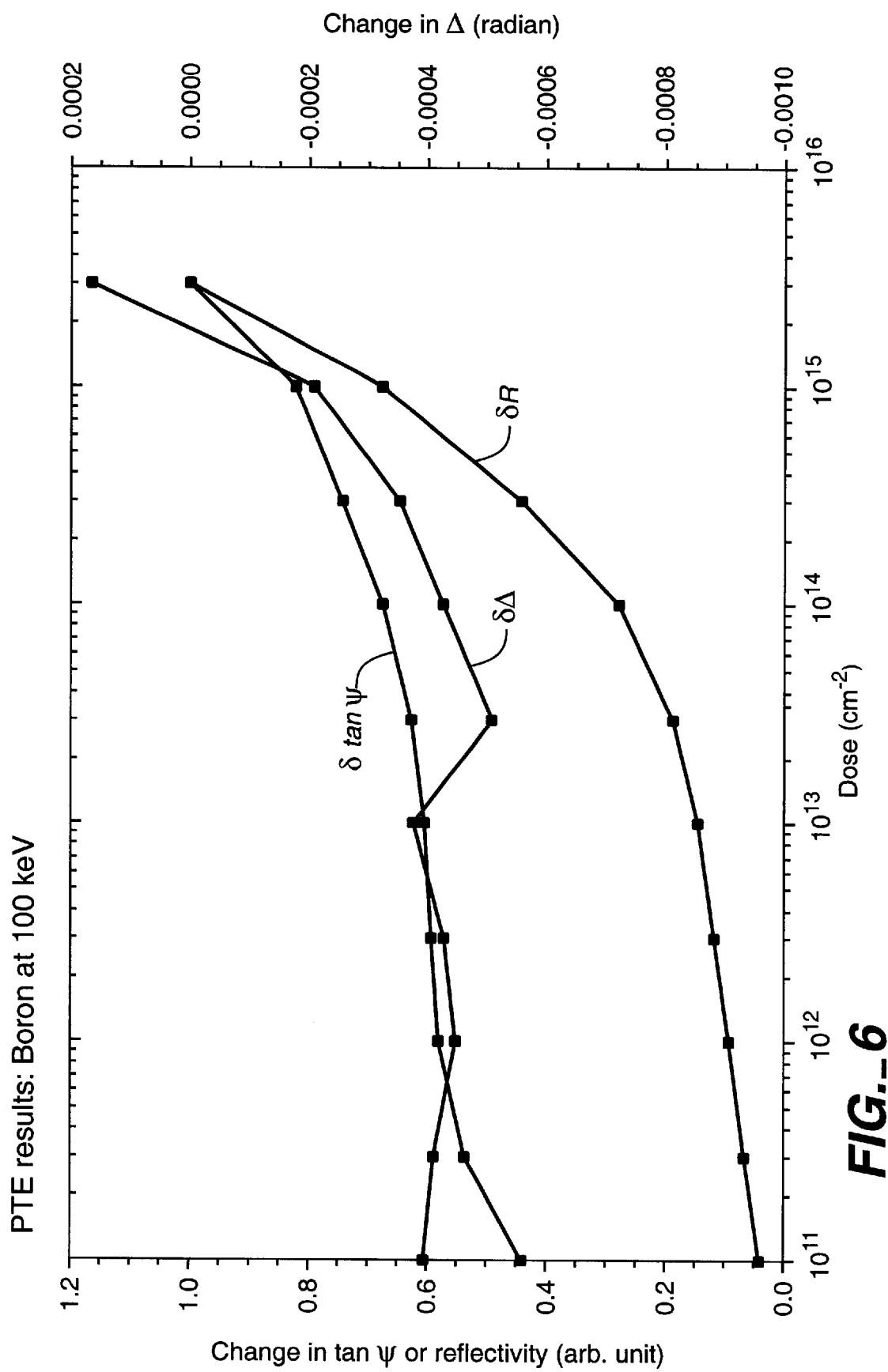
FIG._6

SYSTEM FOR NON-DESTRUCTIVE MEASUREMENT OF SAMPLES

BACKGROUND OF THE INVENTION

This invention relates in general to measurement of samples and in particular, to a system for a non-destructive measurement of properties of a sample. This invention is particularly useful for non-destructive measurement of dose of a dopant in a semiconductor material.

In semiconductor manufacturing, it is frequently desirable to obtain information concerning the properties of a semiconductor material in a sample such as a wafer during or after processing. For example, it may be desirable to obtain an indication of the dose of a dopant in a semiconductor material such as silicon.

One system for measuring dose is proposed in U.S. Pat. No. 4,952,063. As described in this patent, a thermal wave is generated in a material by causing periodic localized heating of the material by focusing an intensity modulated pump beam of light on a spot of the sample surface. A probe beam is directed towards the spot of the sample surface to sense changes in the indices of refraction induced by the pump beam. The output of the detector is processed to analyze reflected light signals that are in phase with the modulation of the pump beam in order to detect changes in reflectivity of the sample. Such reflectivity measurements are then used to determine dopant concentration, residue deposits and defects of samples.

While the system described in U.S. Pat. No. 4,952,063 may be useful for certain dose measurements, it has many disadvantages. Thus, for some dopant concentrations, the change in reflectivity measured may correspond to different values of the dopant concentration so that the dopant concentration cannot be uniquely identified from the change in reflectivity. The change in reflectivity may also be too small to be measured for some dopant concentrations.

Spectroscopic ellipsometry is used to measure the damage profile at high doses. For wafers implanted at low doses, spectroscopic ellipsometry may not be adequate.

In U.S. Pat. No. 5,536,936, a spectroscopic ellipsometer is used to measure the ellipsometric parameter values of the sample in the presence of and in the absence of excitation of the sample. The technique in U.S. Pat. No. 5,536,936, however, lacks adequate sensitivity for measuring the change in ellipsometric parameters caused by excitation of the sample.

None of the above described systems is entirely satisfactory. It is, therefore, desirable to provide an improved system for non-destructive measurement of samples, which avoids the above-described difficulties or disadvantages.

SUMMARY OF THE INVENTION

As noted above, when a pump beam of radiation is supplied to a sample, energy of the beam is absorbed by the sample, thereby causing the physical properties of the sample to change. The change in the physical properties of the sample causes changes in the ellipsometric parameters of the sample. By detecting the change in one or more ellipsometric parameters of the sample caused by the pump beam, physical properties of the sample can be measured. To increase measurement sensitivity, the pump beam is modulated at a first modulation frequency. Physical properties of the sample are thus also modulated at the first frequency. A polarized probe beam is supplied to the sample and modified by the sample to provide a modified beam. Where the pump beam is modulated at the first frequency, the probe beam is also caused by the sample to be modulated at such frequency. A polarization state of radiation in the probe beam is modulated at a second frequency before detection. The modified beam is detected to provide an output. The output is processed to provide information or indication related to a signal at a frequency substantially equal to the difference between the first and the second frequencies or the harmonics thereof in any combination. A change in one or more ellipsometric parameters is derived from such information or indication. Such change is a measure of the physical properties of the sample. By deriving from the detected output signal information of a signal at a difference frequency, the technique of this invention provides adequate sensitivity to obtain a measurable change in one or more ellipsometric parameters of the sample caused by the pump beam.

In a related aspect of the invention, it may be desirable to measure dose of a dopant in a semiconductor wafer, the profile of such dopant, and also measure the film thickness and/or index of refraction information of the wafer by means of the same instrument. Preferably, the instrument includes a device for measuring dose of a dopant in the wafer and a second device for measuring film thickness and/or index of refraction information of the wafer.

BRIEF DESCRIPTION OF THE DRAWINGS

FIG. 1 is a schematic view of an ellipsometer for measuring the change in the structure of a semiconductor material in the sample, such as that caused by dopants, and of a spectroscopic ellipsometer (shown in dotted lines) to illustrate an embodiment of the invention.

FIG. 2 is a block diagram of a signal processing flow diagram to illustrate the operatins of the dose measurement of FIG. 1.

FIGS. 3–6 are graphical plots of the change in ellipsometric parameters and change in reflecting as functions of dose of dopants in the sample to illustrate the invention.

FIG. 7 is a schematic view of an ellipsometer employing a probe beam of multiple wavelengths for measuring the change in the structure of a semiconductor material in the sample, such as that caused by dopants, to illustrate the preferred embodiment of the invention.

FIG. 8 is a block diagram of a combined instrument for measuring dose of dopants and for measuring other physical properties of the sample to illustrate the invention.

For simplicity in description, identical components are identified by the same numerals in this application.

DETAILED DESCRIPTION OF THE PREFERRED EMBODIMENT

FIG. 1 is a schematic view of an ellipsometer for measuring physical properties of a sample such as a semiconductor wafer non-destructively to illustrate the preferred embodiment of the invention. As shown in FIG. 1, system 10 includes a first source for generating a pump beam. When the pump beam generated by the source is absorbed by an area of the wafer, the temperature of the area is increased, and the increase in surface temperature alters the complex index of refraction of the surface. When the wafer has been doped with a dopant, such as through an implantation process, the heat dissipation characteristics of the wafer at the surface area depend on the dose and the implant profile in the damaged layers in the wafer. Such heat dissipation characteristics, in turn, determine the change in temperature of the wafer surface and the change in the complex index of refraction of the surface. The above effects are described more thoroughly in "A New Method of Photothermal Displacement Measurement by Laser Interferometric Probe Its Mechanism and Applications to Evaluation of Lattice Damage in Semiconductors," S. Sumie et al., *Jpn. J. Appl. Phys.* Vol. 31 (1992), pp. 3575–3583. The change in the complex index of refraction results in changes in the ellipsometric parameters of a sample 12. System 10 provides a probe beam for interrogating such changes.

The pump beam 16 is generated by means of an infrared laser 14. Beam 16 is modulated by means of an acousto-optic modulator 18 at a frequency $\omega_a$. The first order modulated beam from laser 14 is reflected by mirror 20 and focused by lens 22 into pump beam 24 towards a spot 12a of sample 12 which may be a semiconductor wafer. As described above, absorption of the energy from pump beam 24 will cause the index of refraction at spot 12a of the sample to change. This, in turn, will result in change in ellipsometric parameters of sample 12 at spot 12a. The change in the ellipsometric parameters would indicate physical properties of sample 12 such as the dose of dopants (e.g. in ion implantation) or other impurities or defects in the sample. The ellipsometric parameters of the sample are influenced by the alteration in the structure in sample 12. Where sample 12 is a doped semiconductor wafer, for example, the change in ellipsometric parameters indicate the alteration in the crystal structure of the semiconductor material resulting from introduction of a foreign material in the structure. If the alteration in the sample structure is caused by doping, then the measure of the degree of alteration in the structure of the sample will indicate indirectly the concentration of dopants. Where the doping is performed by ion implantation, such change will indicate the implant dose in the sample. With the pump beam modulated at frequency $\omega_a$, physical properties of the sample and consequently the ellipsometric parameters are also caused to be modulated at such frequency. The probe beam will therefore also be modulated by the sample at this frequency $\omega_a$.

Pump beam 24 may be a continuous beam or may consist of a sequence of pump pulses. Where pump beam 24 is continuous, modulator 18 modulates the intensity of the beam at frequency $\omega_a$. Where pump beam comprises a continuous stream of pump pulses, modulator 18 may modulate the stream at frequency $\omega_a$ in two different ways. The continuous stream of pulses in beam 16 may be modulated so that a number of the pulses are passed as a burst, where such pump pulse bursts are sent at intervals at frequency $\omega_a$. Alternatively, the pump beam 24 may be modulated to comprise a continuous stream of pump pulses whose intensities are modulated at frequency $\omega_a$. In any event, in the frequency domain, both methods of modulation introduce the same modulation frequency components.

The thermal wavelength $\lambda$ is a measure of heat penetration of a thermal wave caused by the pump beam. The wavelength $\lambda$ is inversely related to the square root of the modulation frequency $\omega_a$ according to the equation below:

$$\lambda = 2\pi \sqrt{\frac{2D}{\omega_a}} \quad (1)$$

where D is the diffusivity of the material in the sample. From the equation above, it is evident that the modulation frequency $\omega_a$ determines the depth of penetration of the thermal wave caused by the pump beam 24. Therefore, by varying the modulation frequency $\omega_a$, the depth for profiling the sample structure of sample 12 may be varied and selected. The zeroth order beam that passes through modulator 18 is collected in a beam dump 26.

As noted above, when the energy of the pump beam 24 is absorbed by sample 12 at spot 12a, the index of refraction of the sample material at such spot is also varied at this frequency, and hence the ellipsometric parameters of the sample are affected also according to this frequency.

The change in ellipsometric parameters are interrogated by means of a probe beam which is supplied by a laser 42. A beam from laser 42 is passed through a linear polarizer 44 and modulated by a photo-elastic modulator (PEM) 46 at frequency $\omega_m$, and focused by lens 48 as a probe beam 50 preferably to spot 12a of the sample.

Radiation from probe beam 50 reflected by sample 12 is collected by a collecting lens 62 and passed through an analyzer 64 and passed through a band pass filter 66 to detector 68. As normal in ellipsometric measurements, either the polarizer 44 or the analyzer 64 is rotated during the measurement. Filter 66 substantially passes radiation of wavelength at or near the wavelength of probe laser 42 to block radiation in the infrared range from pump laser 14 and to improve signal-to-noise ratio. The output of detector 68 is applied to three filters 72, 74, 76. The outputs of the three filters are supplied to a central processing unit 80 for processing. In the embodiment of FIG. 1, it is assumed that radiation reflected from sample 12 is detected. It will be understood, however, that where sample 12 transmits light, the light transmitted through sample 12 may be detected instead by detector 68. Such and other variations are within the scope of the invention.

This invention is based on the observation that detection sensitivity can be much improved by detecting a difference frequency between the two modulation frequencies $\omega_a$ and $\omega_m$ or between any harmonics of the two frequencies in any combination. Unlike the device in U.S. Pat. No. 5,536,936 which lacks adequate sensitivity for detecting the changes in ellipsometric parameters, the technique illustrated in FIG. 1 provides adequate independent information for detecting such change and for deriving from such change the dose of dopants in sample 12.

In a preferred embodiment, filter 72 passes the direct current (DC) component of the output of detector 68, filter 74 has a bandwidth such that it passes substantially only the signal component of frequency $\omega_m-\omega_a$ and band pass filter 76 passes substantially only the signal component at frequency $2\omega_m-\omega_a$ of the output. The output of filter 72 is therefore $I_{DC}$. The outputs of filters 74 and 76 are respectively $I_{\omega_m-\omega_a}$ and $I_{2\omega_m-\omega_a}$.

The pump laser beam 24 modulates the surface temperature of the wafer, which, in turn, changes the complex refractive index and the reflection coefficients $r_s$, $r_p$ of s- and p-polarization of the wafer surface:

$$r_s = r_s^o(1 + m_s \sin\omega_a t) \quad (2)$$

$$r_p = r_p^o(1 + m_p \sin\omega_a t)$$

where $m_p$, $m_s$ are modulation indices which are proportional to the modulated pump intensity. The ellipsometric parameters $\psi$ and $\Delta$ are defined by:

$$\frac{r_p}{r_s} = \tan\psi e^{j\Delta} \quad (3)$$

Where $m_p$, $m_s$ are much smaller than 1, to first order approximation, the changes in ellipsometric parameters become:

$$\delta \tan \psi = \tan \psi \, \text{Re}(m_p - m_s) \quad \delta\Delta = \text{Im}(m_p - m_s) \qquad (4)$$

It will be noted that the quantities $\delta \tan \psi$ and $\delta\Delta$ are Fourier coefficients of the changes at frequency $\omega_a$ in the ellipsometric parameters of the sample caused by the pump beam. Any fluctuations in the absorbed power by the sample other than those due to the modulation by modulator 18 will cause $m_p$, $m_s$ of the equations (4) to change. Thus, it is assumed for the purpose of the equations (4) that the absorbed power is modulated only by modulator 18; it being understood that the undesirable effects of at least some of the other factors that cause variations in absorbed power can be removed by calibration, such as the effects of variations in the intensity of the pump beam, in a manner known to those skilled in the art and will not elaborated here. Detector signal components at DC, $\omega_a$, $\omega_m-\omega_a$ and $2\omega_m-\omega_a$ become:

$$I_{DC} = \frac{1}{4}F(1 + \tan^2\psi) \qquad (5)$$

$$I_{\omega_a} = \frac{1}{2}F\tan^2\psi \text{Re}(m_p - m_s)$$

$$I_{\omega_m - \omega_a} = F\tan\psi J_1(\delta_0)[\sin\Delta \text{Re}(m_p - m_s) + \cos\Delta \text{Im}(m_p - m_s)]$$

$$I_{2\omega_m - \omega_a} = -F\tan^2\psi J_2(\delta_0)\text{Re}(m_p - m_s)$$

where F is the system's response function. One can eliminate the systems response function F by normalizing the detector signal with the DC term:

$$\frac{I_{\omega_a}}{I_{DC}} = 2\sin^2\psi \text{Re}(m_p - m_s) \qquad (6)$$

$$\frac{I_{\omega_m - \omega_a}}{I_{DC}} = 2\sin2\psi J_1(\delta_0)[\sin\Delta \text{Re}(m_p - m_s) + \cos\Delta \text{Im}(m_p - m_s)]$$

$$\frac{I_{2\omega_m - \omega_a}}{I_{DC}} = -4\sin^2\psi J_2(\delta_0)\text{Re}(m_p - m_s)$$

The fact that the detector signal provides adequate information to eliminate the dependence on the system's response function F is one advantage inherent in the invention of this application. This means that system 10 is self-calibrating, and no additional calibration step or equipment is necessary for calibrating system 10. The first and third equations in equations (6) carry the same information regarding $\text{Re}(m_p - m_s)$ so that only one of the two equations is needed. Of the equations in equations (6), only two linear independent equations involving the coefficients of the differences in harmonic frequencies are necessary to determine the changes in the ellipsometric parameters. Of the first and third equations in equations (6), the one for $I_{2\omega_m-\omega_a}$ is chosen for improved signal-to-noise ratio, since signals at the pump modulation frequency $\omega_a$ may leak through to the detector in the detection process. Obviously, coefficients of differences between harmonics higher than those in equations (6) may be filtered and processed instead and are within the scope of this invention. Expressed in terms of ellipsometric parameters, $\psi$ and $\Delta$:

$$\frac{I_{\omega_a}}{I_{DC}} = 2\sin^2\psi \frac{\delta\tan\psi}{\tan\psi} \qquad (7)$$

$$\frac{I_{\omega_m-\omega_a}}{I_{DC}} = 2\sin2\psi J_1(\delta_0)\left[\sin\Delta\frac{\delta\tan\psi}{\tan\psi} + \cos\Delta\delta\Delta\right]$$

$$\frac{I_{2\omega_m-\omega_a}}{I_{DC}} = -4\sin^2\psi J_2(\delta_0)\frac{\delta\tan\psi}{\tan\psi}$$

or $$\begin{pmatrix} \frac{I_{\omega_m-\omega_a}}{I_{DC}} \\ \frac{I_{2\omega_m-\omega_a}}{I_{DC}} \end{pmatrix} = \begin{bmatrix} \frac{2\sin2\psi\sin\Delta J_1(\delta_0)}{\tan\psi} & 2\sin2\psi\cos\Delta J_1(\delta_0) \\ \frac{-4\sin^2\psi J_2(\delta_0)}{\tan\psi} & 0 \end{bmatrix} \begin{pmatrix} \delta\tan\psi \\ \delta\Delta \end{pmatrix} \qquad (8)$$

The pump induced changes in the ellipsometric parameters can be expressed in terms of normalized signals:

$$\begin{pmatrix} \delta\tan\psi \\ \delta\Delta \end{pmatrix} = \qquad (9)$$

$$\frac{\tan\psi}{8\sin2\psi\sin^2\psi\cos\Delta J_1(\delta_0)J_2(\delta_0)} \begin{bmatrix} 0 & -2\sin2\psi\cos\Delta J_1(\delta_0) \\ \frac{4\sin^2\psi J_2(\delta_0)}{\tan\psi} & \frac{2\sin2\psi\sin\Delta J_1(\delta_0)}{\tan\psi} \end{bmatrix}$$

$$\begin{pmatrix} \frac{I_{\omega_m-\omega_a}}{I_{DC}} \\ \frac{I_{2\omega_m-\omega_a}}{I_{DC}} \end{pmatrix}$$

From the above, it is seen that the change in the two ellipsometric parameters $\delta \tan \psi$ and $\delta\Delta$ may be obtained from the outputs of filters 72, 74 and 76. Where a number of calibration wafers with different known implant doses are measured using system 10 to obtain different values of the changes in the ellipsometric parameters $\delta \tan \psi$ and $\delta\Delta$, a lookup table may be compiled correlating the changes in the ellipsometric parameters with the known doses of the ion implants, for each specific type of dopant. Then when a sample 12 doped with a particular dopant of unknown dose is measured using system 10 to obtain the changes in ellipsometric parameters $\delta \tan \psi$ and $\delta\Delta$ as illustrated above, the lookup tables already compiled for such type of dopant may be employed to determine uniquely the dose of the dopant or in sample 12.

The above-described process and the calculations may be performed as illustrated in FIG. 2 which is a signal processing flow chart. As shown in FIG. 2, the output of detector 68 is passed through three filters placed in parallel, whose outputs are applied to processor 80. Processor 80 performs the above calculations on the outputs of the three filters to obtain $\delta \tan \psi$ and $\delta\Delta$ as illustrated in FIG. 2.

FIG. 3 is a graphical plot of the change in $\tan \psi$ and $\delta\Delta$ as a function of dose to illustrate the invention. As noted in FIG. 3, the same change in $\tan \psi$ or $\Delta$ may correspond to more than one value of dose. However, by measuring both the change in $\Delta$ and the change in $\tan \psi$, it is possible to determine a single value for the dose. FIG. 3 illustrates the changes in $\tan \psi$ and $\Delta$ where sample 12 is implanted with phosphorus at 40 keV. Shown also in FIG. 3 is the change in reflectivity R of sample 12 as a function of dose.

FIG. 4 is a graphical plot of the change in $\tan \psi$ and, $\Delta$ and reflectivity R as a function of dose where the dopant is arsenic implanted at 100 keV. As will be noted from FIG. 4, the change $\delta R$ in reflectivity for arsenic is a multi-valued function around $5\times10^{13}/\text{cm}^2$, so that the same change in reflectivity may correspond to two different values of dose. Thus, FIG. 4 clearly illustrates that by measuring only the change in reflectivity as in U.S. Pat. No. 4,952,063, in certain ranges of dose, there may be more than one value of dose corresponding to a value of change in reflectivity, so that the value of the dose cannot be uniquely identified by measuring the change in reflectivity. This is not the case in the present invention where the changes in both tan ψ and Δ are both measured so that the value of dose can be uniquely identified. FIG. 5 illustrates the changes in tan ψ, Δ and reflectivity R where the dopant is boron fluoride at 60 keV. FIG. 6 illustrates the changes in tan ψ, Δ and reflectivity R where the dopant is boron at 100 keV.

While it is desirable to detect at the frequencies of filters 72, 74 and 76 described above, measurements at other frequencies may also yield similar information and can be used to determine the dose of the dopant. As can be seen from equations (5) for $I_{\omega_a}$ and for $I_{2\omega_m-\omega_a}$, these two signal components contain the same information. Thus, instead of passing the signal component at $2\omega_m-\omega_a$, filter 76 may instead pass a signal component at frequency $\omega_a$ instead, although $2\omega_m-\omega_a$ is probably at a lower frequency than $\omega_a$ and would be easier to process. Such output of filter 76 may be combined with the unchanged outputs of filter 72 and 74 to yield δ tan ψ and δΔ. In still other embodiments, one or more of the filters 72, 74 and 76 may be omitted and still useful information may be obtained to indicate dose of the dopant. Thus, a single filter 74 or 76 may be adequate for some applications for determining the dose of the dopant. As used in this application, the difference between harmonics of a first and a second frequency would include the difference between any multiple of the first frequency and any multiple of the second frequency, where one times the first or the second frequency is a multiple of such frequency.

As described above, the depth beyond the surface of the sample 12 that is penetrated by the thermal wave caused by the pump beam 24 depends upon the thermal wavelength which, in turn, depends upon the modulation frequency introduced by modulator 18. Therefore, the depth for profiling the structure, such as the doped structure of a semiconductor material, may be varied by varying the modulation frequency $\omega_a$ introduced by modulator 18. If the probe beam 50 includes radiation components of multiple wavelengths, measurements at the frequencies of these components in the manner described above will yield different values for the changes in ellipsometric parameters from which dose and depth profile of the dopant can be derived. For this purpose, laser 42 is replaced by a radiation source supplying radiation at multiple wavelengths, such as a broadband source in the form of a xenon arc lamp, for example.

A broadband system 100 is shown in FIG. 7. As shown in FIG. 7, as in FIG. 1, a pump laser beam 24 modulated at frequency $\omega_a$ is supplied to surface area 12a of sample 12 as in FIG. 1. Instead of using a probe laser, a white light source such as xenon lamp 142 is used. Radiation of source 142 is focused by mirror 144, polarized by polarizer 44 and modulated by means of PEM 46 at frequency $\omega_m$ and directed to preferably surface area 12a. As described above, the portion of sample 12 at or near surface area 12a is thermally affected by the pump beam 24 so that physical properties of such portion of the wafer is also modulated at frequency $\omega_a$. The probe beam 150 is therefore modulated by the sample at the pump beam frequency $\omega_a$ as well and the probe beam so modulated is passed through an analyzer 64 and reflected and focused by mirror 152 to a detector 160. In one embodiment, detector 160 may comprise a spectrometer which includes a diffraction element such as a prism or grating 162 and an array of detectors 164. Alternatively, detector 160 may include a monochromator to select a wavelength component that is passed to a detector for detecting the intensity of such component. The output(s) of the detector or the array of detectors are then supplied to filters such as filters 72–76 of FIG. 1 and the filtered signals are then supplied to a processor for processing. The filters and the processor are omitted from FIG. 7 to simplify the drawing. In such manner, the changes in the ellipsometric parameters δ tan ψ and δΔ may be derived at each wavelength of the wavelength components that are being detected by detector 160.

As in other ellipsometric measurements, either the polarizer 44 or the analyzer 64 is rotated during the measurement. In system 100, the probe beam 150 is focused by mirror 144 before it is polarized by fixed polarizer 44. It may be preferable to reverse the order of the two elements so that the probe beam 150 is first polarized by polarizer 44 and modulated by PEM 46 before it is focused by mirror 144 to area 12a of the sample. In the manner described above, the dose of the dopant and depth profile of the dopant may be computed.

In many applications, it may be desirable to measure a number of parameters of the sample in the same setting. Thus, in addition to measuring the dose of a dopant in sample 12, it may also be desirable to measure the thickness (es) and/or indices of refraction of one or more layers of sample 12. For this purpose, another ellipsometer 100, in addition to system 10, may be employed such as indicated in dotted lines in FIG. 1. Thus, as shown in FIG. 1, a broadband light source such as a xenon lamp 102 supplies a broadband radiation beam 104 which is polarized by a polarizer (not shown) and then focused by mirror 106 to spot 12a. Preferably, the beam 104 is focused to spot 12a when the pump beam 24 is not supplied to the same spot. The radiation from beam 104 reflected by sample 12 is passed through an analyzer (not shown), collected and/or focused by mirrors 110 and 112 and applied to a spectrometer 114. The polarizer or analyzer is rotated during the measurement. To simplify the figure, the polarizer and analyzer normally employed in ellipsometers have been omitted in FIG. 1. From the output of spectrometer 114, the thickness(es) and the indices of refraction of one or more layers on sample 12 may be determined by means of a processor (not shown).

Typically, the user would perform measurements of the thickness(es) and/or indices of refraction using system 100 before or after the dose measurement using system 10 as described above. Instead of using a spectroscopic ellipsometer 100 as described above in conjunction with system 10 as shown in FIG. 1, a reflectometer, polarimeter, or single wavelength ellipsometer may be used instead in conjunction with system 10 to perform the same measurement.

A more general configuration is illustrated conceptually in FIG. 7. Thus, system 10' and the additional measurement instrument 100' together would form a combined instrument for measuring the dose and dose profile of dopants and of thickness(es) and/or indices of refraction of one or more layers of the same sample 12. System 10' of FIG. 7 may be the same as system 10 of FIG. 1.

Instead of using system 10 of FIG. 1 in conjunction with an ellipsometer or reflectometer in a combined instrument as described above, it is also possible to use a different system for system 10' in FIG. 7 for measuring dose. For example, the system described in U.S. Pat. No. 4,952,063 may be used in conjunction with an ellipsometer, a reflectometer or polarimeter to perform such measurements. Such and other variations are summarized in FIG. 7 and are within the scope of the invention. In U.S. Pat. No. 4,952,063, a modulated pump beam is applied to the sample in the same manner as that described above for system 10 of FIG. 1. A probe beam, which can be polarized or unpolarized, is then applied to the same spot of the sample that is heated by the pump beam and the reflected or transmitted probe beam from the sample is then detected by a photodetector, also analogous to system 10 of FIG. 1. Instead of detecting and analyzing different frequencies as described above for system 10, the technique in U.S. Pat. No. 4,952,063 employs a processor for analyzing intensity variations of such reflected or transmitted probe beam where such variations are in phase with the periodic changes of the pump beam to indicate the presence of residues, defects as well as levels of ion dopants concentrations in semiconductors.

In the description above in reference to FIG. 1, the detector signal output is filtered by means of three filters 72, 74 and 76 and the outputs of the filters are then processed by processor 80. Filters 74 and 76 may be implemented by means of lock-in amplifiers locking in at difference frequencies $\omega_m - \omega_a$ and $2\omega_m - \omega_a$, respectively. Alternatively, it may be possible to first digitize the outputs of detector 68 and provide the digitized signals to processor 80 where processor 80 derives information or indication related to the intensity or amplitudes of signals at frequencies $\omega_m - \omega_a$ and $2\omega_m - \omega_a$. This alternative may also have the advantage that the differences between more harmonics of the two frequencies present in the detector output may be processed and calculated for determining the dose and dose profile of the sample. Such and other variations are within the scope of the invention.

While the invention has been described above by reference to various embodiments, it will be understood that changes and modifications may be made without departing from the scope of the invention, which is to be defined only by the appended claims and their equivalents. All of the references mentioned in the description above are hereby incorporated in their entirety by reference.

What is claimed is:

1. A method for non-destructively measuring properties of a sample, comprising:

supplying at least one pump beam of radiation to a surface area of the sample, the intensity of said pump beam varying at at least a first modulation frequency, so that physical properties of the sample are modulated at the first frequency;

directing a polarized probe beam of radiation so that the probe beam is modulated at the first frequency by the sample;

modulating a polarization state of radiation in the probe beam at at least a second frequency;

providing, in response to radiation from the probe beam that has been modulated by the sample and that has been modulated at at least the second frequency, information related to a signal at a difference frequency substantially equal to the difference between the first and the second frequencies or between harmonics of the two frequencies in any combination; and deriving a change in one or more ellipsometric parameters of the sample from the indication.

2. The method of claim 1, wherein said providing comprises detecting radiation from the probe beam that has been modulated by the sample and that has been modulated at at least the second frequency to provide an output, and filtering the output to provide a signal having the difference frequency.

3. The method of claim 1, said sample having a structure that has been altered, said method further comprising determining a degree of alteration of the sample structure from the change in ellipsometric parameters of the surface from the indication.

4. The method of claim 3, said sample having a semiconductor structure that has been altered by being doped with a dopant, said method further comprising determining a concentration of the dopant from the change in ellipsometric parameters of the surface.

5. The method of claim 4, said sample having a semiconductor structure that has been altered by being implanted with an ion implant, said method further comprising determining a dose of the implant in the sample from the change in ellipsometric parameters of the surface.

6. The method of claim 4, wherein said directing directs radiation of multiple wavelengths, said detecting detects at two or more of said wavelengths, said deriving derives changes in one or more ellipsometric parameters at said two or more of said wavelengths, and said determining determines a depth profile of the dopant in the sample.

7. The method of claim 4, further comprising varying the first frequency to vary a depth for profiling the structure.

8. The method of claim 1, wherein said deriving derives from the indication information related to a signal component at a frequency substantially equal to the difference between the first and second frequencies.

9. The method of claim 8, wherein said deriving also derives from the indication information related to a signal component at a frequency substantially equal to the difference between the first frequency and the second or higher harmonic of the second frequency.

10. The method of claim 8, wherein said deriving derives from the indication information related to a signal component at a frequency substantially equal to the first frequency.

11. The method of claim 8, wherein said deriving also derives information related to a DC component from said indication.

12. The method of claim 1, wherein said supplying supplies a substantially continuous pump beam or a sequence of pump pulses.

13. The method of claim 12, wherein said supplying includes modulating a continuous stream of pulses at the first modulation frequency.

14. The method of claim 1, wherein said probe beam is modulated at the second frequency before or after its modification by the sample.

15. The method of claim 1, wherein said first and second frequencies are in a range of about 0.1 Hz to 10 GHz.

16. The method of claim 1, wherein said directing directs a probe beam of multiple wavelengths.

17. A method for non-destructively measuring properties of a semiconductor sample having a dopant, comprising:

measuring dose of the dopant in the sample by means of an instrument; and measuring film thickness and/or index of refraction information of the sample by means of the instrument, wherein said dose measuring includes:

supplying at least one pump beam of radiation to a surface area of the sample;

varying the intensity of said pump beam at at least a first modulation frequency, so that physical properties of the sample are modulated at the first frequency;

directing a polarized probe beam of radiation so that the probe beam is modulated by the sample at the first frequency;

modulating a polarization state of radiation in the probe beam at at least a second frequency;

providing, in response to radiation from the probe beam that has been modulated by the sample and that has been modulated at at least the second frequency, an indication related to a signal at a difference frequency substantially equal to the difference between the first and the second frequencies or between harmonics of the two frequencies in any combination; and deriving a change in one or more ellipsometric parameters of the sample from the indication.

18. The method of claim 17, further comprising determining a dose of the dopant in the sample from the change in ellipsometric parameters of the sample.

19. The method of claim 17, wherein said deriving derives from the indication information related to a signal component at a frequency substantially equal to the difference between the first and second frequencies.

20. The method of claim 19, wherein said deriving derives also information related to a signal component at a frequency substantially equal to the difference between the first frequency and the second or higher harmonic of the second frequency.

21. The method of claim 19, wherein said deriving also derives information related to a DC component of said output.

22. The method of claim 17, wherein said probe beam is modulated at the second frequency before or after its modification by the sample.

23. The method of claim 17, wherein said first and second frequencies are in a range of about 0.1 Hz to 10 GHz.

24. The method of claim 17, wherein said supplying supplies a substantially continuous pump beam or a sequence of pump pulses.

25. The method of claim 24, wherein said supplying includes modulating a continuous stream of pulses at the first modulation frequency.

26. The method of claim 17, wherein said directing directs a probe beam of multiple wavelengths.

27. The method of claim 17, wherein said providing comprises detecting radiation from the probe beam that has been modulated by the sample and that has been modulated at at least the second frequency to provide an output, and filtering the output to provide a signal having the difference frequency.

28. The method of claim 17, wherein said dose measuring includes:

supplying at least one pump beam of radiation to a surface area of the sample;

varying the intensity of said pump beam at at least a modulation frequency, so that physical properties of the sample are modulated at the modulation frequency;

directing a probe beam of radiation so that the probe beam is modulated by the sample at the modulation frequency;

detecting radiation in the probe beam after its modification by the sample to provide an output; and deriving the dose of the dopant from the output.

29. The method of claim 28, wherein said deriving includes analyzing a signal in the output that is substantially in phase with the modulation frequency.

30. The method of claim 17 wherein said dose measuring further includes:

varying the intensity of said pump beam at at least a first modulation frequency, so that physical properties of the sample are modulated at the first frequency;

directing a probe beam of radiation so that the probe beam is modulated by the sample at the first frequency;

providing, in response to radiation from the probe beam that has been modulated by the sample, a change in one or more parameters of the sample; and determining a dose of the dopant in the sample from the change in said one or more parameters of the sample.

31. The method of claim 17, wherein said film thickness and/or index of refraction information of the sample is measured by measuring ellipsometric parameters.

32. The method of claim 17, wherein said film thickness and/or index of refraction information of the sample is measured when dose is not measured.

33. The method of claim 17, wherein the two measurements are performed on substantially the same area of the sample.

34. A apparatus for non-destructively measuring properties of a sample, comprising:

a first source supplying at least one pump beam of radiation to a surface area of the sample, the intensity of said pump beam varying at at least a first modulation frequency, so that physical properties of the sample are modulated at the first frequency;

a second source supplying a polarized probe beam of radiation so that the probe beam is modulated by the sample at the first frequency;

a modulator modulating a polarization state of radiation in the probe beam at at least the second frequency;

a detector detecting radiation from the probe beam that has been modulated by the sample and that has been modulated at at least the second frequency to provide an output; and a processor deriving from the output an indication related to a signal at a frequency substantially equal to the difference between the first and the second frequency or between harmonics of the two frequencies in any combination and a change in one or more ellipsometric parameters of the sample from the indication.

35. The apparatus of claim 34, said sample having a structure that has been altered, said processor determining a degree of alteration of the sample structure from the change in ellipsometric parameters of the surface from the output.

36. The apparatus of claim 35, said sample having a semiconductor structure that has been altered by being doped with a dopant, said processor determining a concentration of the dopant from the change in ellipsometric parameters of the surface from the output.

37. The apparatus of claim 36, said sample having a semiconductor structure that has been altered by being implanted with an ion implant, said processor determining a dose of the implant in the sample from the change in ellipsometric parameters of the surface from the output.

38. The apparatus of claim 37, said sample including a semiconductor containing an ion implant, said processor further determining a dose of the implant in the sample from the change in ellipsometric parameters of the surface from the output.

39. The apparatus of claim 38, wherein said second source supplies radiation of multiple wavelengths, said detector detects at two or more of said wavelengths, and said processor derives changes in one or more ellipsometric parameters at said two or more of said wavelengths, and determines a depth profile of the implant in the sample.

40. The apparatus of claim 36, wherein said first source varies the first frequency to vary a depth for profiling the dopant in the structure.

41. The apparatus of claim 34, wherein said processor derives information related to a signal at a frequency substantially equal to the difference between the first and second frequencies.

42. The apparatus of claim 41, wherein said processor derives information related to a signal also at a frequency substantially equal to the difference between the first frequency and the second or higher harmonic of the second frequency.

43. The apparatus of claim 41, wherein said processor derives information related to a signal also at a frequency substantially equal to the first frequency.

44. The apparatus of claim 41, wherein said processor derives information related to a DC component of said output.

45. The apparatus of claim 34, wherein said first source supplies a substantially continuous pump beam or a sequence of pump pulses.

46. The apparatus of claim 45, wherein said first source modulates a continuous stream of pulses at the first modulation frequency.

47. The apparatus of claim 34, further comprising a modulator modulating said probe beam at the second frequency before or after its modification by the sample.

48. The apparatus of claim 42, said modulator including a photo-elastic modulator, a electro-optic modulator, a magneto-optic modulator, Faraday rotator, liquid crystal retarder or spectrum analyzer.

49. The apparatus of claim 34, wherein said second frequency is in a range of about 0.1 Hz to 10 GHz.

50. The apparatus of claim 34, wherein said second source supplies a probe beam of multiple wavelengths.

51. The apparatus of claim 34, wherein said processor includes a filter that provides a signal in response to the output.

52. An apparatus for non-destructively measuring properties of a semiconductor sample having a dopant, comprising
a first device measuring dose of the dopant in the sample; and
a second device measuring film thickness and/or index of refraction information of the sample;
wherein said first device includes:
 a first source supplying at least one pump beam of radiation to a surface area of the sample;
 a modulator varying the intensity of said pump beam at at least a first modulation frequency, so that physical properties of the sample are modulated at the first frequency;
 a second source directing a polarized probe beam of radiation so that the probe beam is modulated by the sample at the first frequency, and a modulator modulating a polarization state of radiation in the probe beam at at least a second frequency prior to or after its modification by the sample.

53. The apparatus of claim 52, wherein the second device includes an ellipsometer or reflectometer measuring the film thickness and/or index of refraction information.

54. The apparatus of claim 52, wherein said obtaining means further includes a detector detecting radiation from the modulated probe beam after it has been modulated by the sample to provide an output, and a processor processing the output to provide information concerning dose of the dopant.

55. The apparatus of claim 54, wherein the processor derives information related to a signal at a frequency substantially equal to the difference between the first and the second frequencies or between harmonics of the two frequencies in any combination from the output, wherein the processor derives a change in one or more ellipsometric parameters of the surface area from the output.

56. The apparatus of claim 55, wherein said processor derives information related to a signal at a frequency substantially equal to the difference between the first and second frequencies.

57. The apparatus of claim 56, wherein said processor also derives information related to a signal at a frequency substantially equal to the difference between the first frequency and the second or higher harmonic of the second frequency.

58. The apparatus of claim 56, wherein said processor also derives information related to a signal detects a DC component of said output.

59. The apparatus of claim 56, wherein said first and second frequencies are in a range of about 0.1 Hz to 10 GHz.

60. The apparatus of claim 52, wherein said modulator varies the first frequency to vary a depth for profiling the structure.

61. The apparatus of claim 52, wherein said first source supplies a substantially continuous pump beam or a sequence of pump pulses.

62. The apparatus of claim 52, wherein said first device includes:
means for applying at least one pump beam of radiation to a surface area of the sample;
a modulator varying the intensity of said pump beam at at least a modulation frequency, so that physical properties of the sample are modulated at the modulation frequency;
means for supplying a probe beam of radiation so that the probe beam is modulated by the sample at the first frequency;
a detector detecting radiation in the probe beam after its modification by the sample to provide an output; and
a processor deriving the dose of the dopant from the output.

63. The apparatus of claim 62, wherein said processor analyzes a signal in the output that is substantially in phase with the modulation frequency.

64. A combination apparatus for non-destructively measuring properties of a semiconductor sample having a dopant, comprising
a first device measuring dose of the dopant in the sample; and
a second device different from the first device measuring film thickness and/or index of refraction information of the sample;
wherein said first device includes:
 a first source supplying at least one pump beam of radiation to a surface area of the sample
 a modulator varying the intensity of said pump beam at at least a first modulation frequency, so that physical properties of the sample are modulated at the first frequency;
 a second source directing a polarized probe beam of radiation so that the probe beam is modulated by the sample at the first frequency, and a modulator modulating a polarization state of radiation in the probe beam at at least a second frequency prior to or after its modification by the sample.

65. The apparatus of claim 64, wherein the second device includes an ellipsometer or reflectometer measuring the film thickness and/or index of refraction information.

66. The apparatus of claim 64, wherein said first device further includes:
a detector detecting radiation from the modulated probe beam after it has been modulated by the sample to provide an output; and a processor processing the output to provide information concerning dose of the dopant.

67. The apparatus of claim 64, wherein the second device includes a broadband spectroscopic ellipsometer and the first device includes a single wavelength ellipsometer.

68. A method for non-destructively measuring properties of a semiconductor sample having a dopant, comprising:

measuring dose of the dopant in the sample by means of an instrument; and measuring film thickness and/or index of refraction information of the sample by means of the instrument, wherein said dose measuring includes:

supplying at least one pump beam of radiation to a surface area of the sample;

varying the intensity of said pump beam at at least a first modulation frequency, so that physical properties of the sample are modulated at the first frequency;

directing a polarized probe beam of radiation so that the probe beam is modulated by the sample at the first frequency;

modulating a polarization state of radiation in the probe beam at at least a second frequency before or after it is modulated by the sample;

detecting the probe beam after it has been modulated by the sample and at at least the second frequency; and deriving a change in one or more ellipsometric parameters of the sample from the detected output.

69. The method of claim 68, wherein said detecting includes providing, in response to radiation from the probe beam that has been modulated by the sample and that has been modulated at at least the second frequency, an indication related to a signal at a difference frequency substantially equal to the difference between the first and the second frequencies or between harmonics of the two frequencies in any combination.

* * * * *